United States Patent
Woodward

(10) Patent No.: US 10,573,155 B2
(45) Date of Patent: Feb. 25, 2020

(54) CLOSED LOOP ALARM MANAGEMENT

(71) Applicant: Covidien LP, Mansfield, MA (US)

(72) Inventor: Jonathan James Woodward, Annapolis, MD (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 16/170,512

(22) Filed: Oct. 25, 2018

(65) Prior Publication Data

US 2019/0180592 A1 Jun. 13, 2019

Related U.S. Application Data

(60) Provisional application No. 62/595,628, filed on Dec. 7, 2017.

(51) Int. Cl.
*G08B 21/04* (2006.01)
*G16H 40/63* (2018.01)

(52) U.S. Cl.
CPC ......... *G08B 21/0453* (2013.01); *G16H 40/63* (2018.01)

(58) Field of Classification Search
CPC ........ A61B 5/0022; A61B 5/746; G08B 1/08; G08B 21/0211; G08B 21/0453; G08B 29/10; G16H 40/63
See application file for complete search history.

(56) References Cited

U.S. PATENT DOCUMENTS

| | | | | |
|---|---|---|---|---|
| 2006/0220881 A1* | 10/2006 | Al-Ali | ............... | A61B 5/14552 340/573.1 |
| 2008/0300572 A1* | 12/2008 | Rankers | ............. | A16B 5/14532 604/504 |
| 2011/0105854 A1* | 5/2011 | Kiani | .................... | G16H 40/63 600/300 |
| 2013/0045685 A1* | 2/2013 | Kiani | .................... | G08B 21/24 455/41.2 |
| 2013/0267791 A1* | 10/2013 | Halperin | ............... | A61B 5/002 600/300 |
| 2014/0135588 A1* | 5/2014 | Al-Ali | .................... | G16H 40/63 600/300 |
| 2016/0314260 A1* | 10/2016 | Kiani | .................... | G08B 21/24 |
| 2017/0228508 A1 | 8/2017 | Cook et al. | | |

OTHER PUBLICATIONS

International Search Report dated Jan. 28, 2019 for PCT Application No. US2018/057769 from European Patent Office.

* cited by examiner

*Primary Examiner* — Sisay Yacob

(57) ABSTRACT

Methods, systems, and devices for patient monitoring are described. The method may include receiving an alarm indication associated with a default alarm threshold for a measured physiological parameter and detecting that a clinician is accessing the medical device in response to the alarm indication. After detecting that the clinician is accessing the medical device, the medical device may display an alarm message associated with the alarm indication. The method may further include storing an intervention action associated with an action of the clinician in response to the alarm indication.

20 Claims, 12 Drawing Sheets

CLOSED LOOP ALARM MANAGEMENT

CROSS REFERENCES

The present Application for Patent claims priority to U.S. Provisional Patent Application No. 62/595,628 by Woodward et al., entitled "Closed Loop Alarm Management", filed Dec. 7, 2017, assigned to the assignee hereof.

BACKGROUND

The following relates generally to patient monitoring, and more specifically to closed loop alarm management.

In a healthcare facility such as a hospital, physiological parameters of a patient (e.g., heart rate, respiratory rate, blood pressure) may be monitored by one or more medical devices. For various reasons, such medical devices may sound a false alarm (e.g., inaccurate sensor placement, contributory factors unknown to the medical device, or default alarm thresholds that are inappropriate for a particular patient). A single patient may be monitored by several medical devices, and each device may trigger dozens of false alarms each day. The volume of false alarms from several patients on a daily basis may lead to alarm fatigue and may result in clinicians spending less time caring for their patients. Alarm fatigue may also contribute to reduced response time or ignoring alarms, which may adversely impact the quality of patient care. In the case of a false alarm, a clinician may respond to the alarm, determine that the alarm was indeed false, and may manually deactivate the alarm. However, if the parameters of the alarm remain the same, a similar false alarm will likely reoccur, causing the clinician to repeat this process.

SUMMARY

The described features generally relate to methods, systems, devices, or apparatuses that support closed loop alarm management. A data aggregator may receive an alarm associated with a default alarm setting for a measured parameter of a patient. In some examples, the data aggregator may be next to the patient wearing the medical device or sensor. The data aggregator may communicate with a device worn by the clinician or may otherwise determine the proximity of the clinician to the data aggregator. The data aggregator may detect that a clinician is accessing the medical device. For example, when the clinician is within a threshold proximity to the data aggregator, the data aggregator may activate (i.e., unlock the display screen), so the clinician can record the action taken (e.g., an intervention action) to address the alarm.

Multiple intervention actions may be entered over time by the clinician and may be aggregated to determine a relationship between certain intervention actions and the accuracy of the alarms that triggered the intervention action. Such relationships may be used by clinicians to determine which alarms were false alarms and which were true alarms. Clinicians can then use this data to determine how modifying default alarm settings for a patient will affect the number of false alarms for that patient. In some cases, the aggregated intervention actions may be used to determine a medical compliance and timeliness associated with the clinician.

A method for patient monitoring is described. The method may include receiving, at a medical device, an alarm indication associated with a default alarm threshold for a measured physiological parameter. The method may also include detecting that a clinician is accessing the medical device in response to the alarm indication. The method may also include displaying an alarm message associated with the alarm indication based at least in part on the detecting. Additionally, the method may include storing an intervention action associated with an action of the clinician in response to the alarm indication.

An apparatus for patient monitoring is described. The apparatus may include a processor, memory in electronic communication with the processor, and instructions stored in the memory. The instructions may be executable by the processor to cause the apparatus to receive, at a medical device, an alarm indication associated with a default alarm threshold for a measured physiological parameter. The instructions may be further executable by the processor to cause the apparatus to detect that a clinician is accessing the medical device in response to the alarm indication. The instructions may be further executable by the processor to cause the apparatus to display an alarm message associated with the alarm indication based at least in part on the detecting. Additionally, the instructions may be further executable by the processor to cause the apparatus to store an intervention action associated with an action of the clinician in response to the alarm indication.

Another apparatus for patient monitoring is described. The apparatus may include means for receiving, at a medical device, an alarm indication associated with a default alarm threshold for a measured physiological parameter. The apparatus may further include means for detecting that a clinician is accessing the medical device in response to the alarm indication and means for displaying an alarm message associated with the alarm indication based at least in part on the detecting. Additionally, the apparatus may further include means for storing an intervention action associated with an action of the clinician in response to the alarm indication.

A non-transitory computer-readable medium storing code for patient monitoring is described. The code may include instructions executable by a processor to receive, at a medical device, an alarm indication associated with a default alarm threshold for a measured physiological parameter. The code may further include instructions executable by the processor to detect that a clinician is accessing the medical device in response to the alarm indication and display an alarm message associated with the alarm indication based at least in part on the detecting. Additionally, the code may further include instructions executable by the processor to store an intervention action associated with an action of the clinician in response to the alarm indication.

Some examples of the method, apparatuses, and non-transitory computer-readable medium described herein may further include operations, features, means, or instructions for detecting that the clinician is within a proximity threshold of the medical device, where displaying the alarm message is based at least in part on the proximity detection.

Some examples of the method, apparatuses, and non-transitory computer-readable medium described herein may further include operations, features, means, or instructions for aggregating a plurality of intervention actions stored in response to a plurality of alarm indications associated with the default alarm threshold of the measured physiological parameter. Some examples of the method, apparatuses, and non-transitory computer-readable medium described herein may further include operations, features, means, or instructions for determining a first range of values of the measured physiological parameter associated with a first type of intervention action of the plurality of intervention actions.

Some examples of the method, apparatuses, and non-transitory computer-readable medium described herein may further include operations, features, means, or instructions for determining a second range of values of the measured physiological parameter associated with a second type of intervention action of the plurality of intervention actions.

Some examples of the method, apparatuses, and non-transitory computer-readable medium described herein may further include operations, features, means, or instructions for determining an amount of reduction of a number of instances of the second type of intervention action in the second range of values based at least in part on modifying the default alarm threshold to a modified alarm threshold. Some examples of the method, apparatuses, and non-transitory computer-readable medium described herein may further include operations, features, means, or instructions for determining an effect of modifying the default alarm threshold to the modified alarm threshold based at least in part on determining the amount of reduction of the number of instances of the second type of intervention action.

Some examples of the method, apparatuses, and non-transitory computer-readable medium described herein may further include operations, features, means, or instructions for receiving, at the medical device, a subsequent alarm indication associated with the default alarm threshold for the measured physiological parameter. Some examples of the method, apparatuses, and non-transitory computer-readable medium described herein may further include operations, features, means, or instructions for refraining from displaying an alarm message associated with the subsequent alarm indication based at least in part on the modified alarm threshold. Some examples of the method, apparatuses, and non-transitory computer-readable medium described herein may further include operations, features, means, or instructions for starting a timer after detecting the subsequent alarm indication. Some examples of the method, apparatuses, and non-transitory computer-readable medium described herein may further include operations, features, means, or instructions for alarming according to the default alarm threshold if the subsequent alarm indication is present when a duration of the timer expires.

In some examples of the method, apparatuses, and non-transitory computer-readable medium described herein, the first type of intervention action comprises an action message and the second type of intervention action comprises a no action message. In some examples of the method, apparatuses, and non-transitory computer-readable medium described herein, the aggregated plurality of intervention actions comprises a histogram, wherein the histogram comprises information related to an alarm type and an intervention action type.

Some examples of the method, apparatuses, and non-transitory computer-readable medium described herein may further include operations, features, means, or instructions for determining performance information associated with the clinician based at least in part on the aggregated plurality of intervention actions. In some examples of the method, apparatuses, and non-transitory computer-readable medium described herein, the performance information comprises a response time, an efficiency of the clinician, a service level report, a staff roster report, or a combination thereof.

In some examples of the method, apparatuses, and non-transitory computer-readable medium described herein, displaying the alarm message may include operations, features, means, or instructions for unlocking a display screen of the medical device based at least in part on the detecting that the clinician is within the proximity threshold of the medical device. Some examples of the method, apparatuses, and non-transitory computer-readable medium described herein may further include operations, features, means, or instructions for locking a display screen of the medical device based at least in part on detecting that the clinician exceeded the proximity threshold of the medical device. In some examples of the method, apparatuses, and non-transitory computer-readable medium described herein, the intervention action comprises a routine check, a no action message, or an action message.

In some examples of the method, apparatuses, and non-transitory computer-readable medium described herein, detecting that the clinician is within the proximity threshold of the medical device may include operations, features, means, or instructions for detecting near field communications signaling, detecting Bluetooth signaling, detecting imaging signaling of the clinician, or a combination thereof.

Certain aspects of the present disclosure may include some, all, or none of the above advantages or features. One or more other technical advantages or features may be readily apparent to those skilled in the art from the figures, descriptions, and claims included herein. Moreover, while specific advantages or features have been enumerated above, various examples may include all, some, or none of the enumerated advantages or features.

Further scope of the applicability of the described methods and systems will become apparent from the following detailed description, claims, and drawings. The detailed description and specific examples are given by way of illustration only, since various changes and modifications within the spirit and scope of the description will become apparent to those skilled in the art.

DETAILED DESCRIPTION

In a healthcare facility, one or more medical devices may monitor physiological parameters of a patient. These measurement devices may send medical data and alarm notifications to a data aggregator, which may be a tablet or similar device within a patient's room. If one of the monitoring devices sounds an alarm, a clinician may come into the room to check on the patient. For example, if the alarm is a true alarm (e.g., actually indicative of a physiological decline), the clinician may take some action to address the underlying physiological issue (e.g., administer a drug, etc.). If however the alarm is a false alarm, the clinician may instead manually reset or otherwise turn off the alarm. The data aggregator may determine that an alarm is sounding and may unlock its display screen after detecting that the clinician is accessing the medical device. In some cases, the data aggregator may unlock the display screen based on sensing that the clinician is within a certain proximity. The user interface of the data aggregator may correspond to the alarm and may present options for the clinician to record the action taken in response to the alarm. Accordingly, the clinician may contemporaneously address the alarm while recording the corresponding action. The closed loop alarm response information gathered in this way by the data aggregator may be used by clinicians to adjust alarm thresholds to correspond to the particular needs of certain patients.

In some examples, the closed loop alarm management system may be used to collaborate between multiple alarms or change the default alarm threshold of the respective medical devices. Changing a default alarm threshold may reduce the number of false alarms that a clinician has to address, which may allow the clinician to focus on the real alarms for a patient. Therefore, the closed loop alarm management system may generate less false alarms and further modify the current alarms of interest.

Aspects of the disclosure are initially described in the context of a patient monitoring system. Aspects of the disclosure are further illustrated by and described with reference to apparatus diagrams, system diagrams, and flowcharts that relate to closed loop alarm management.

Figure 1:
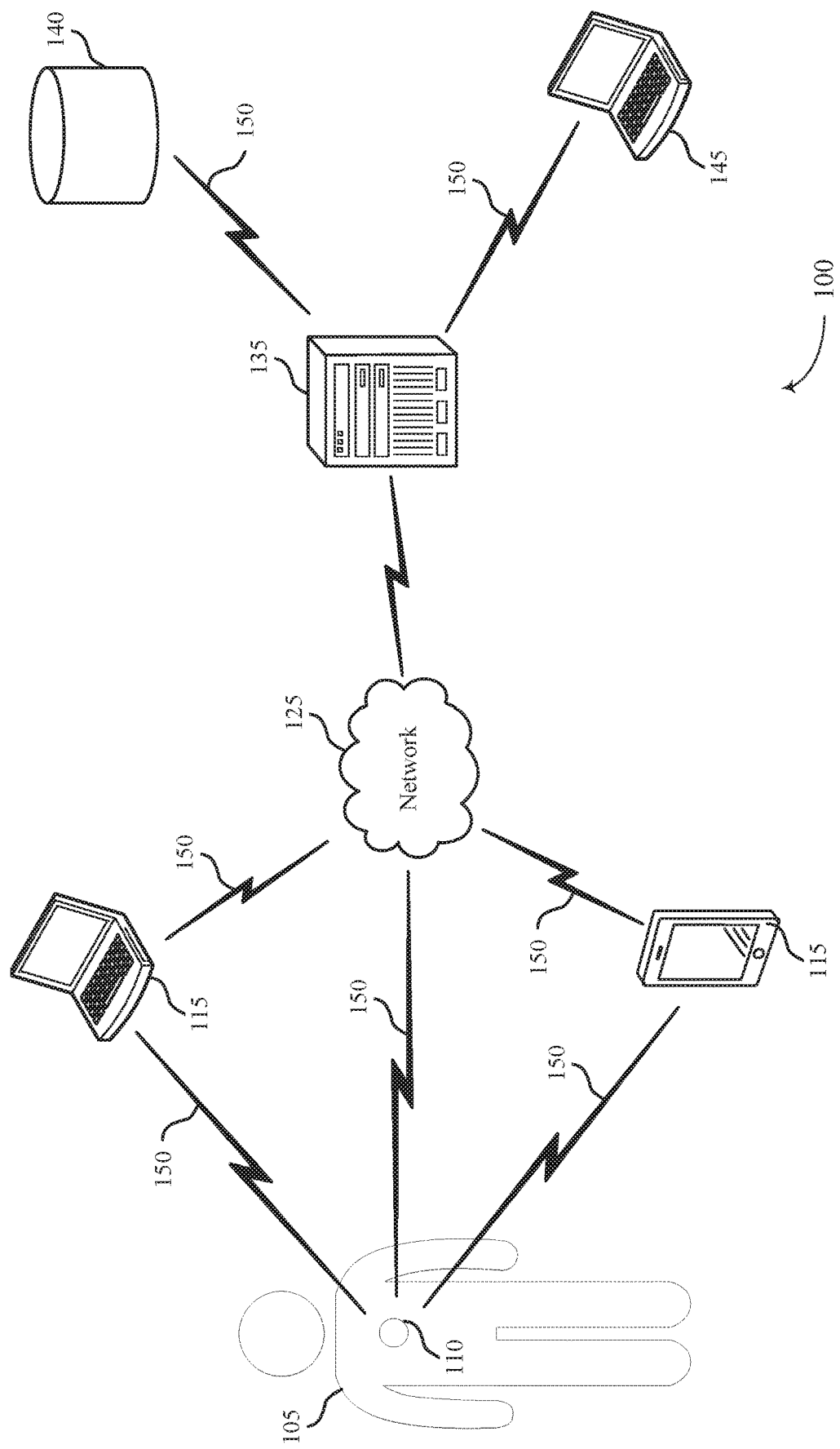
FIG. 1 illustrates an example of a system for patient monitoring that supports closed loop alarm management in accordance with aspects of the present disclosure.

FIG. 1 illustrates an example of a patient monitoring system 100 in accordance with various aspects of the present disclosure. The patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wired or wireless communications links 150 to computing devices 115 or to a network 125.

The medical device 110 may include one or more sensors configured to collect a variety of physiological parameters as well as information related to the location and movement of the patient 105. For example, the medical device 110 may include a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). The data collected by the medical device 110 may be transmitted to either the computing devices 115 or to the remote computing device 145 (via the network 125 and central station 135). Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.). Wired data transmissions may occur over Ethernet connections or any other appropriate wired data connection type.

Computing device 115 may be a wireless device such as a tablet, cellular phone, personal digital assistant (PDA), a dedicated receiver, or other similar device or a spatially distributed network of devices configured to receive signals from the medical device 110. In some cases, computing device 115 may be a wireless laptop computer, a clinician Workstation on Wheels, or a smart hospital bed configured to receive signals from the medical device 110. The computing devices 115 may be in communication with a central station 135 via network 125.

The medical device 110 may also communicate directly with the central station 135 via the network 125. The central station 135 may be a server or a central nurse station located within the hospital or in a remote location. The central station 135 may be in further communication with one or more remote computing devices 145, thereby allowing a clinician to remotely monitor the patient 105. The central station 135 may also be in communication with various remote databases 140 where the collected patient data may be stored. In some cases, the remote databases 140 include electronic medical records (EMR) applications for storing and sharing patient data.

A computing device 115 may be an example of a data aggregator as described herein. In accordance with aspects of the present disclosure, a computing device 115 may receive an alarm indication associated with a default threshold for a measured physiological parameter. The alarm indication may be sent from a medical device 110. The computing device 115 may detect that a clinician is accessing medical device 110. In some cases, the computing device 115 may detect that the clinician is within a proximity threshold of the computing device 115 and may display an alarm message associated with the alarm indication based on detecting the clinician. The computing device 115 may then store one or more intervention actions associated with the action taken by the clinician in response to the alarm indication. Based on the closed loop alarm response information gathered by a computing device 115, a clinician may modify an alarm threshold of the medical device 110 either directly at the medical device 110 or through the computing device 115.

Figure 2:
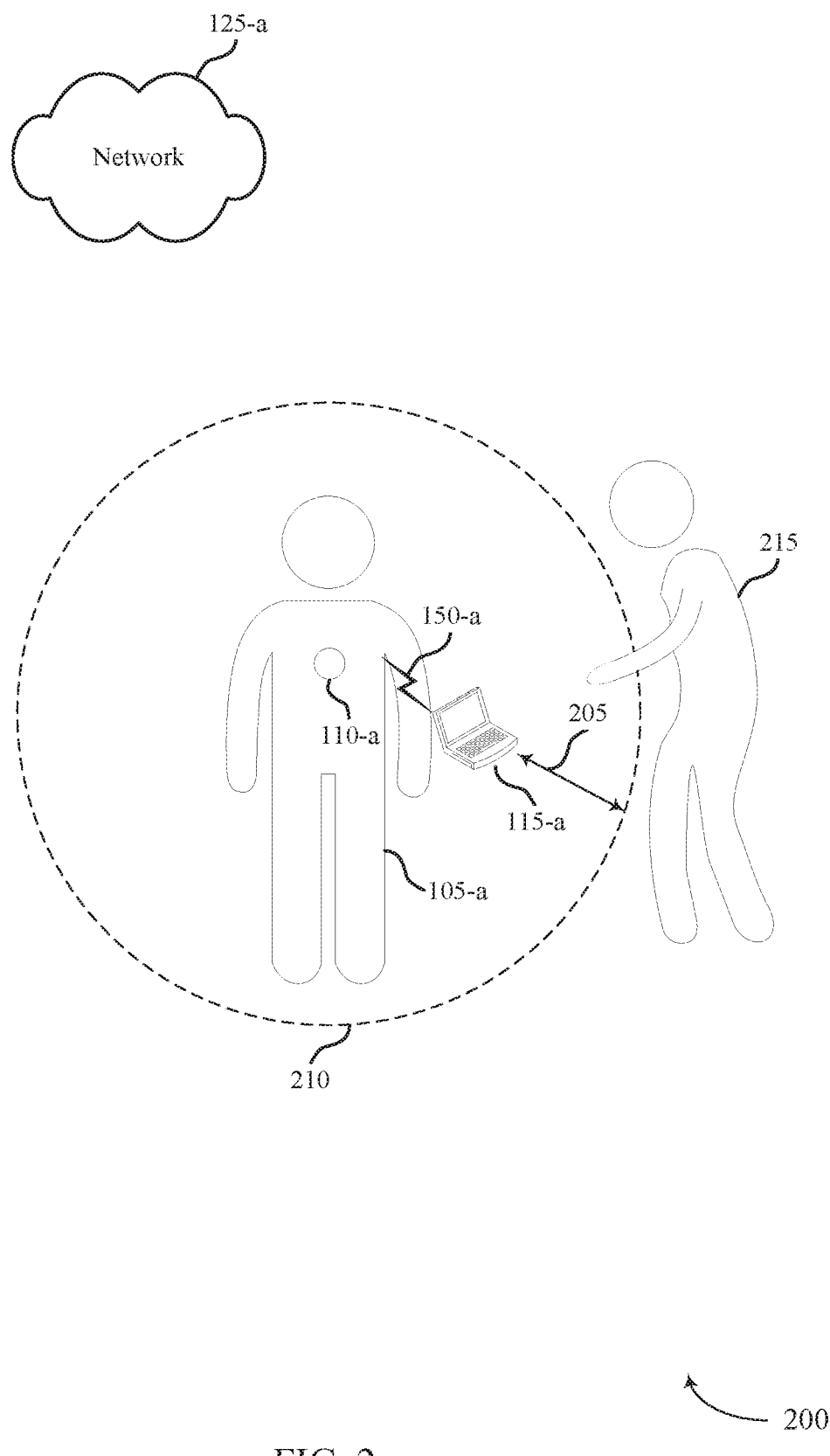
FIG. 2 illustrates an example of a patient monitoring system that supports closed loop alarm management in accordance with aspects of the present disclosure.

FIG. 2 illustrates an example of a patient monitoring system 200 that supports closed loop alarm management in accordance with aspects of the present disclosure. The patient monitoring system 200 includes a medical sensor 110-*a*, which may be an example of medical device 110 described with reference to FIG. 1. The patient monitoring system 200 may also include a data aggregator 115-*a* which may be an example of a local computing device 115 described with reference to FIG. 1. Medical sensor 110-*a* and data aggregator 115-*a* may each be capable of communicating with network 125-*a*, which may be an example of a network 125 described with reference to FIG. 1.

Data aggregator 115-*a* may receive data collected by medical sensor 110-*a*. Data aggregator 115-*a* may receive the data collected by medical sensor 110-*a* directly from medical sensor 110-*a* or from network 125-*a*. In some cases, data aggregator 115-*a* may receive the data from medical sensor 110-*a* and pass it on to the network 125-*a*. Data aggregator 115-*a* may also receive the medical data collected by medical sensor 110-*a* directly from medical sensor 110-*a* (e.g., via communication link 150-*a*) or from a remote server (e.g., via network 125-*a*). In some cases, data aggregator 115-*a* may also receive medical data associated with patient 105-*a* that is collected by medical sensors other than medical sensor 110-*a*. For example, data aggregator 115-*a* may receive medical data for patient 105-*a* from a remote server (e.g., via network 125-*a*).

Medical sensor 110-*a* may collect medical (e.g., physiological) data associated with patient 105-*a*. Medical sensor 110-*a* may store the medical data, and, in some cases, transmit the medical data to network 125-*a*. Medical sensor 110-*a* may also transmit the medical data to data aggregator 115-*a* via communication link 150-*a*. Data aggregator 115-*a* may be near the patient 105-*a* (e.g., at the bedside), or within the patient's room, or within the patient's zone within a healthcare facility.

The medical sensor 110-*a* may detect an alarm condition of patient 105-*a* based on measured medical data. The medical sensor 110-*a* may transmit the alarm condition or some other indication of the alarm to data aggregator 115-*a* via communication link 150-*a*. The alarm condition may be associated with a default alarm condition threshold. That is, the alarm condition may be detected when the alarm condition exceeds or falls below the default alarm condition threshold. Data aggregator 115-*a* may also transmit the alarm condition to network 125-*a*.

In some cases, data aggregator 115-*a* may detect that clinician 215 is accessing the data aggregator 115-*a*. For example, clinician 215 may input a passcode into data aggregator 115-*a* to access the display screen. In other examples, data aggregator 115-*a* may detect clinician's 215 access, and then clinician 215 may input an action to silence an alarm in response to an alarm indication. That is, data aggregator 115-*a* may detect that clinician 215 is responding to an alarm indication.

In some examples, data aggregator 115-*a* may also detect the proximity of clinician 215. For example, data aggregator 115-*a* may determine that clinician 215 is within the threshold distance 205 from data aggregator 115-*a*. In some cases, the threshold distance 205 may define a coverage area of medical sensor 110-*a* in which data aggregator 115-*a* may determine whether or not to activate a display screen based on the proximity of clinician 215. In some examples, the threshold distance (and corresponding coverage area) may be from the perspective of data aggregator 115-*a*. Regardless of which device serves as the origin of the coverage area corresponding to the threshold distance, the threshold distance may represent the distance between two sources (e.g., data aggregator 115-*a* and clinician 215) in which an alarm message is displayed.

Data aggregator 115-*a* may detect the proximity of clinician 215 through a variety of detection techniques. For example, data aggregator 115-*a* may detect that clinician 215 is within the threshold distance 205 using near field communication signaling, Bluetooth signaling (e.g., Bluetooth low energy (BTLE) beacon signaling), image signaling of clinician 215 (e.g., video recognition of clinician), or a combination thereof. In some examples, the clinician may wear or carry a device that facilitates the threshold distance calculation by the data aggregator 115-*a*. For example, the clinician 215 may carry a smart watch or smart phone that supports BTLE signaling.

In the example depicted in FIG. 2, data aggregator 115-*a* may determine the proximity of clinician 215 (e.g., data aggregator 115-*a* may determine that clinician 215 is within threshold distance 205, or within coverage area 210). Based on this determination, data aggregator 115-*a* may display an alarm message. The alarm message may be associated with the alarm condition received by data aggregator 115-*a*. In some cases, the alarm message may be displayed by unlocking a display screen of data aggregator 115-*a*. Unlocking the display screen may prompt clinician 215 to input medical data associated with patient 105-*a*. After data aggregator 115-*a* determines the proximity of clinician 215, the display screen may unlock and a selection window may be displayed. Therefore, clinician 215 may access the display screen without using log in credentials. In addition, unlocking the display screen my prompt clinician to input an intervention action. The display screen may also display patient parameters and a plurality of stored intervention actions. The clinician can enter the intervention action directly into the data aggregator 115-*a* or via another device (e.g., a smart watch or smart phone).

In some cases, data aggregator 115-*a* may determine that clinician 215 exceeds threshold distance 205, or is outside coverage area 210. In such cases, data aggregator 115-*a* may lock the display screen based on clinician 215 exceeding threshold distance 205 of data aggregator 115-*a*.

An intervention action may be associated with the action taken by clinician 215 in response to the transmitted alarm condition of medical sensor 110-*a*. For example, clinician 215 may input an intervention action of routine check if the clinician 215 assess patient 105-*a* under a routine action (e.g., checking vitals, changing bedding, etc.). In some cases, clinician 215 may input an action message if the clinician 215 performs an action in response to the alarm condition (e.g., administering a drug to patient 105-*a*). In some examples, clinician 215 may input a no action message if the clinician 215 performs no action on the patent 105-*a* in response to the alarm condition (e.g., the clinician 215 turns off or otherwise suppresses the alarm).

Data aggregator 115-*a* may store the intervention actions inputted by clinician 215 over time. In some cases, the clinician may input one or more intervention actions associated with the one or more alarm conditions. Data aggregator 115-*a* may then aggregate the one or more intervention actions. In some cases, data aggregator 115-*a* may display the aggregated intervention actions as a histogram. For example, the histogram may include information related to the type of alarm or the type of intervention action.

In some cases, the aggregated intervention actions may determine the performance of clinician 215 in response to the alarm condition, including a medical compliance and timeliness associated with clinician 215. For example, the aggregated intervention actions may determine a response time of clinician 215 or an efficiency of clinician 215. In some cases, the aggregated intervention actions may additionally produce a staff level report or a staff roster report. The performance of clinician 215 may be displayed through the user interface of data aggregator 115-*a*.

The aggregated intervention actions may be used to modify the default alarm threshold and determine an effect of the modified alarm threshold (e.g., how the number of false alarms would be reduced if the default alarm threshold was modified by a certain amount). Storing the intervention actions may provide information to facilitate adjustment of an alarm threshold of a medical sensor 110-*a*. That is, the clinician may configure data aggregator 115-*a* and/or a particular medical sensor 110-*a* to function as a "smart alarm."

After a smart alarm has been configured for a particular medical sensor 110-*a* for a particular patient 105-*a*, the medical sensor 110-*a* may transmit a subsequent alarm condition to data aggregator 115-*a* via communication link 150-*a*. The subsequent alarm condition may also be associated with the default alarm threshold of medical sensor 110-*a*. However, data aggregator 115-*a* may refrain from displaying the alarm message associated with the subsequent alarm condition. That is, the alarm message may be based on the modified alarm threshold rather than the default alarm threshold. For example, data aggregator 115-*a* may receive indication to alarm that would have caused an alarm under the default alarm threshold, but does not cause an alarm under the modified alarm threshold (e.g., smart alarm threshold).

However as a failsafe mode, in some examples the data aggregator 115-*a* may start a timer after a subsequent alarm condition is detected under the smart alarm configuration (e.g., an alarm condition that does not trigger an alarm due to the modified alarm threshold, but that would have trigger an alarm under the default threshold). Medical sensor 110-*a* may alarm according to the default alarm threshold if the subsequent alarm condition is still present when the duration of the timer expires. Such a timer may act as a failsafe mode to ensure that a perceived false alarm is indeed false. That is, if the condition that triggered the perceived false alarm is still present after some threshold period of time, this may indicate that the underlying condition causing the alarm is real, and that an alarm should actually be sound.

Figure 3:
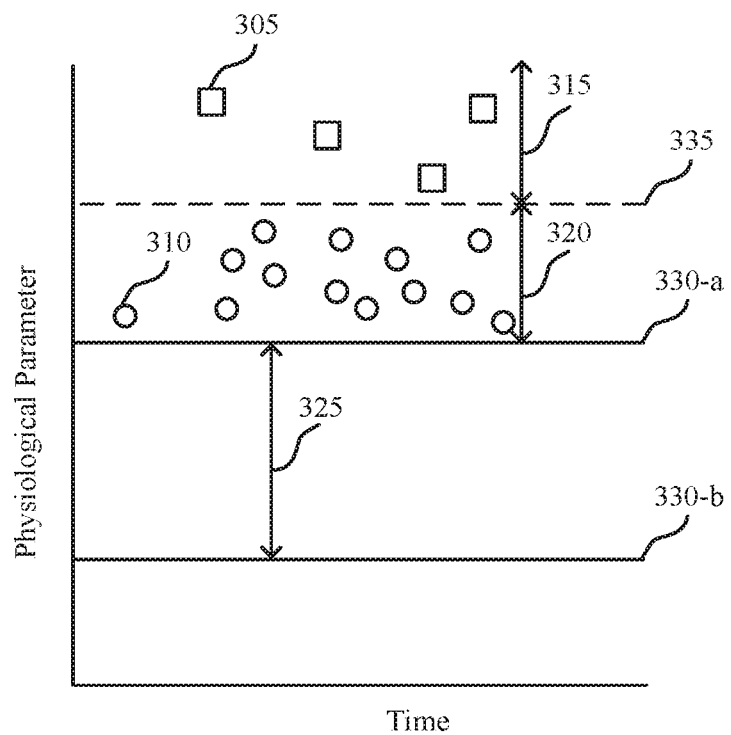
FIG. 3 illustrates an example diagram that supports closed loop alarm management in accordance with aspects of the present disclosure.

FIG. 3 illustrates an example diagram 300 that supports closed loop alarm management in accordance with aspects of the present disclosure. The X axis represents time, and the Y axis represents the values of a physiological parameter being measured by a medical device (e.g., medical sensor 110-*a* of FIG. 2). The diagram 300 also illustrates instances of different types of intervention actions (e.g., intervention actions 305, 310) recorded by a clinician at a data aggregator in response to an alarm condition.

Range 325 may correspond to a "normal" range of values for the particular physiological parameter being measured. That is, measured values of the physiological parameter falling within range 325 will not trigger an alarm at a medical device. Range 325 may be defined by a higher default alarm threshold 330-*a* and a lower default alarm threshold 330-*b*. These default alarm thresholds 330-*a*, 330-*b* may be configured on a medical device by the device manufacturer, or may be manually configured by a clinician.

If the measured physiological parameter falls above higher default alarm threshold 330-*a*, the corresponding medical device may sound an alarm, and a clinician may address the alarm and record a corresponding intervention action in response to the alarm, as described with reference to FIG. 2. Over a given period of time (e.g., a nurse's shift, a day, a week, etc.), several of these intervention actions may be recorded at a data aggregator and displayed at the data aggregator (or another device) in a manner represented by diagram 300. It should be noted that diagram 300 illustrates only one example of how the relationship between different types of intervention actions and the corresponding alarm condition (e.g., the value of the parameter triggering the alarm) can be graphically represented. For example, diagram 300 could instead be illustrated as a histogram.

Intervention actions 310 may correspond to "no action" intervention actions. For example, a "no action" intervention action may be an example of a clinician addressing an alarm by simply turning off the alarm (e.g., after determining that no actual medical attention is needed). Intervention actions 305 may instead correspond to "action" intervention actions. An "action" intervention action may be an example of a clinician responding to an alarm by taking some medical action (e.g., administering a drug, performing a procedure, etc.). As described above, a "no action" intervention action may be indicative of a false alarm, whereas an "action" intervention action may be indicative of a true alarm.

As illustrated by diagram 300, the instances of "no action" intervention actions 310 and "action" intervention actions 305 may cluster together with respect to the values of the physiological parameter that triggered the alarm (e.g., along the Y axis of the diagram 300). Such a clustering may indicate that the higher default alarm threshold 330-*a* is set too high for this particular patient, which may cause several instances of false alarms. In such cases, to reduce the number of false alarms, the higher default alarm threshold 330-*a* may be adjusted to a modified alarm threshold 335. Adjusting the default alarm threshold 330-*a* may be an example of configuring a medical device with a smart alarm threshold.

A medical device (e.g., a data aggregator) may automatically modify a default alarm threshold based on an identified statistical relationship between the different types of intervention actions. For example, data aggregator 115-*a* may determine a number of instances of "no action" intervention actions 310 within a range 320. That is, the data aggregator 115-*a* may determine a range 320 of the measured physiological values that are associated with the "no action" intervention actions 310. Based on the number of instances of a "no action" intervention action 310 within this range 320, the medical device may adjust the higher default alarm threshold 330-*a* to a modified alarm threshold 335. A medical device may also determine a number of instances of an "action" intervention action 305 that fall within a particular range 315. Adjusting the higher default alarm threshold 330-*a* to the modified alarm threshold 335 may be based on the identification of each of these ranges 315, 320 and identifying a boundary between them. Such an adjustment may reduce the number of false alarms for that patient associated with the particular physiological parameter because measured values falling within range 320 will no longer trigger an alarm. In some examples, some other device communicatively coupled with the medical sensor (e.g., a central station) may adjust the default alarm threshold 330-*a*.

In some examples, the data aggregator may determine an effect of modifying default alarm threshold 330-*a* to modified alarm threshold 335. In other words, the data aggregator may determine an amount of reduction in the instances of the "no action" intervention actions 310 if the modified alarm threshold 335 were implemented. This predicted effect of modifying an alarm threshold may be presented by the data aggregator in graphical form, or a suggestion message, or otherwise conveyed to a clinician. The clinician may use this information to implement various smart alarms for a particular patient in an effort to reduce false alarms.

Figure 4:
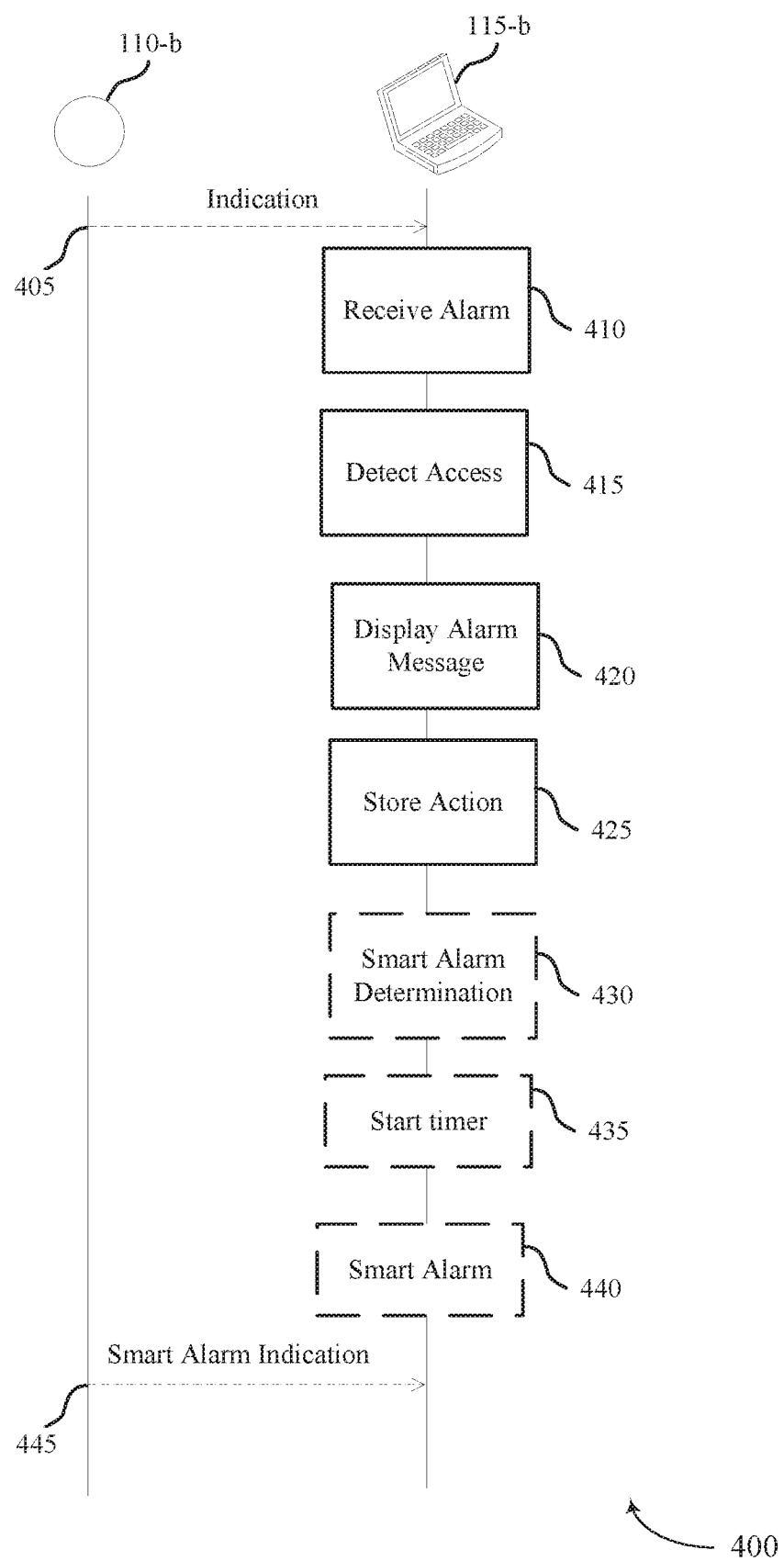
FIG. 4 illustrates an example process flow that supports closed loop alarm management in accordance with aspects of the present disclosure.

FIG. 4 illustrates an example process flow 400 that supports closed loop alarm management in accordance with aspects of the present disclosure. Process flow 400 may include medical sensor 110-*b* and data aggregator 115-*b*, which may be respective examples of a medical device 110 and computing device 115 as described in reference to FIGS. 1 and 2. Data aggregator 115-*b* may be one or more other medical devices, local computing devices, or remote computing devices. Alternative examples of the following may be implemented, where some steps are performed in a different order or not at all. Some steps may additionally include additional features not mentioned above.

Medical sensor 110-*b* may transmit an indication 405 to notify data aggregator 115-*b* of an alarm. At block 410, data aggregator 115-b may receive the alarm indication (e.g., alarm condition). In some cases, the alarm indication may be associated with a default alarm threshold for a measured physiological parameter (e.g., measured medical data).

At block 415, data aggregator 115-b may detect that a clinician is accessing the medical device (e.g., data aggregator 115-b). In some examples, detecting that the clinician is accessing the medical device may be in response to an alarm indication. In some cases, data aggregator 115-b may detect that the clinician is within a proximity threshold (e.g., threshold distance 205) of the medical device. Data aggregator 115-b may detect that the clinician is within the proximity threshold of the medical device by detecting near field communications signaling, detecting Bluetooth signaling, detecting imaging signaling of the clinician, or a combination thereof.

At block 420, data aggregator 115-b may display an alarm message associated with the alarm indication (e.g., indication 405) based at least in part on detecting the proximity of the clinician. In some cases, displaying the alarm message may include unlocking a display screen of the medical device (e.g., data aggregator 115-b) based on detecting that the clinician is within the proximity threshold of the medical device (e.g., data aggregator 115-b). In some examples, data aggregator 115-b may lock the display screen based on detecting that the clinician exceeded the proximity threshold of the medical device (e.g., data aggregator 115-b).

At block 425, data aggregator 115-b may store an intervention action associated with an action of the clinician in response to the alarm indication (e.g., indication 405). In some cases, the intervention action may include a routine check, a no action message, or an action message.

At block 430, a smart alarm determination may occur. For example, data aggregator 115-b may aggregate a plurality of intervention actions stored in response to a plurality of alarm indications (e.g., indication 405) associated with the default alarm threshold of the measured physiological parameter. In some examples, the aggregated plurality of intervention actions may include a histogram. For example, the histogram may include information related to an alarm type and an intervention action type. In some cases, the aggregated plurality of intervention actions may determine performance information associated with the clinician. For example, performance information may include a response time, an efficiency of the clinician, a service level report, a staff roster report, or a combination thereof.

In some examples, data aggregator 115-b may determine a first range of values (e.g., real alarms) of the measured physiological parameter associated with a first type of intervention action (e.g., "action" intervention action) of the plurality of intervention actions at block 430. At block 430, data aggregator 115-b may also determine a second range of values (e.g., false alarms) of the measured physiological parameter associated with a second type of intervention action (e.g., "no action" intervention action) of the plurality of intervention actions. For example, the first type of intervention action may be an action message, and the second type of intervention action may be a no action message.

As part of the smart alarm determination at block 430, data aggregator 115-b may determine an amount of reduction of a number of instances of the second type of intervention action in the second range of values based on modifying the default alarm threshold to a modified alarm threshold. At block 430, data aggregator 115-b may also determine an effect of modifying the default alarm threshold to the modified alarm threshold based on determining the amount of reduction of the number of instances of the second type of intervention action. As described with reference to FIGS. 2 and 3, based on these determinations made by the data aggregator 115-b, the data aggregator 115-b may implement a smart alarm either automatically or in response to manual inputs from a clinician.

At block 435, data aggregator 115-b may start a timer. The timer may start after detecting a subsequent alarm indication (e.g., indication 405). At block 440, data aggregator 115-b may alarm according to the default alarm threshold if the subsequent alarm indication is present when a duration of the timer expires.

Medical sensor 110-b may transmit a smart alarm indication 445 to notify data aggregator 115-b of a smart alarm. For example, data aggregator 115-b may receive a subsequent alarm indication (e.g., smart alarm indication 445) associated with the default alarm threshold for the measured physiological parameter. In some cases, data aggregator 115-b may refrain from displaying an alarm message associated with the subsequent alarm indication (e.g., subsequent alarm condition) based on a modified alarm threshold.

Figure 5:
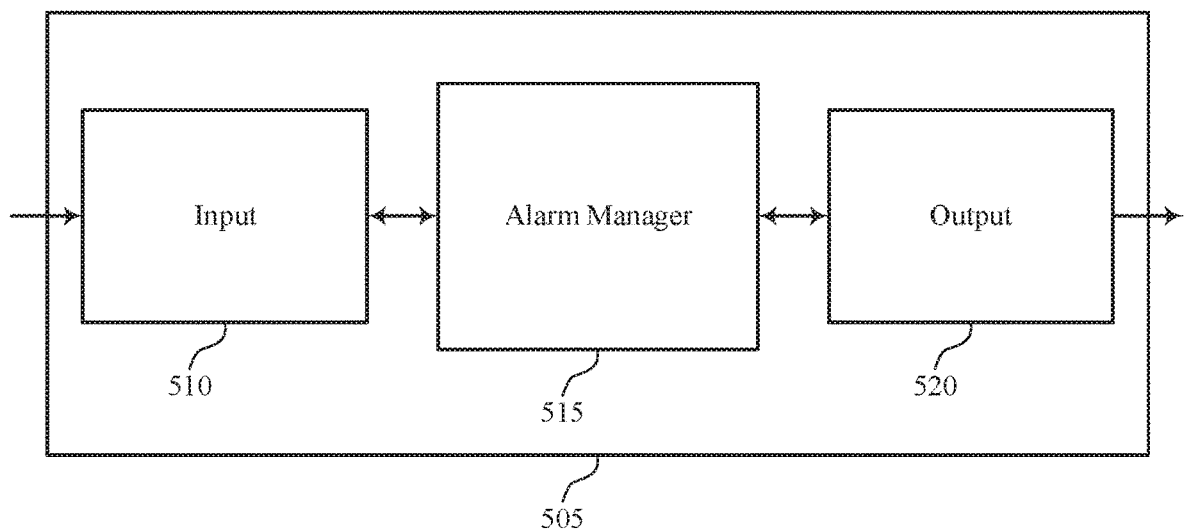
FIGS. 5 through 7 show block diagrams of a device that supports closed loop alarm management in accordance with aspects of the present disclosure.

FIG. 5 shows a block diagram 500 of a device 505 that supports closed loop alarm management in accordance with aspects of the present disclosure. Device 505 may be an example of aspects of a medical device as described herein. Device 505 may include input 510, alarm manager 515, and output 520. Device 505 may also include a processor. Each of these components may be in communication with one another (e.g., via one or more buses).

Alarm manager 515 and/or at least some of its various sub-components may be implemented in hardware, software executed by a processor, firmware, or any combination thereof. If implemented in software executed by a processor, the functions of the alarm manager 515 and/or at least some of its various sub-components may be executed by a general-purpose processor, a digital signal processor (DSP), an application-specific integrated circuit (ASIC), an field-programmable gate array (FPGA) or other programmable logic device, discrete gate or transistor logic, discrete hardware components, or any combination thereof designed to perform the functions described in the present disclosure. The alarm manager 515 and/or at least some of its various sub-components may be physically located at various positions, including being distributed such that portions of functions are implemented at different physical locations by one or more physical devices. In some examples, alarm manager 515 and/or at least some of its various sub-components may be a separate and distinct component in accordance with various aspects of the present disclosure. In other examples, alarm manager 515 and/or at least some of its various sub-components may be combined with one or more other hardware components, including but not limited to an I/O component, a transceiver, a network server, another computing device, one or more other components described in the present disclosure, or a combination thereof in accordance with various aspects of the present disclosure.

Alarm manager 515 may receive, at a medical device, an alarm indication associated with a default alarm threshold for a measured physiological parameter and detect that a clinician is accessing the medical device in response to the alarm indication. Alarm manager 515 may also display an alarm message associated with the alarm indication based on the detecting and store an intervention action associated with an action of the clinician in response to the alarm indication.

Figure 6:
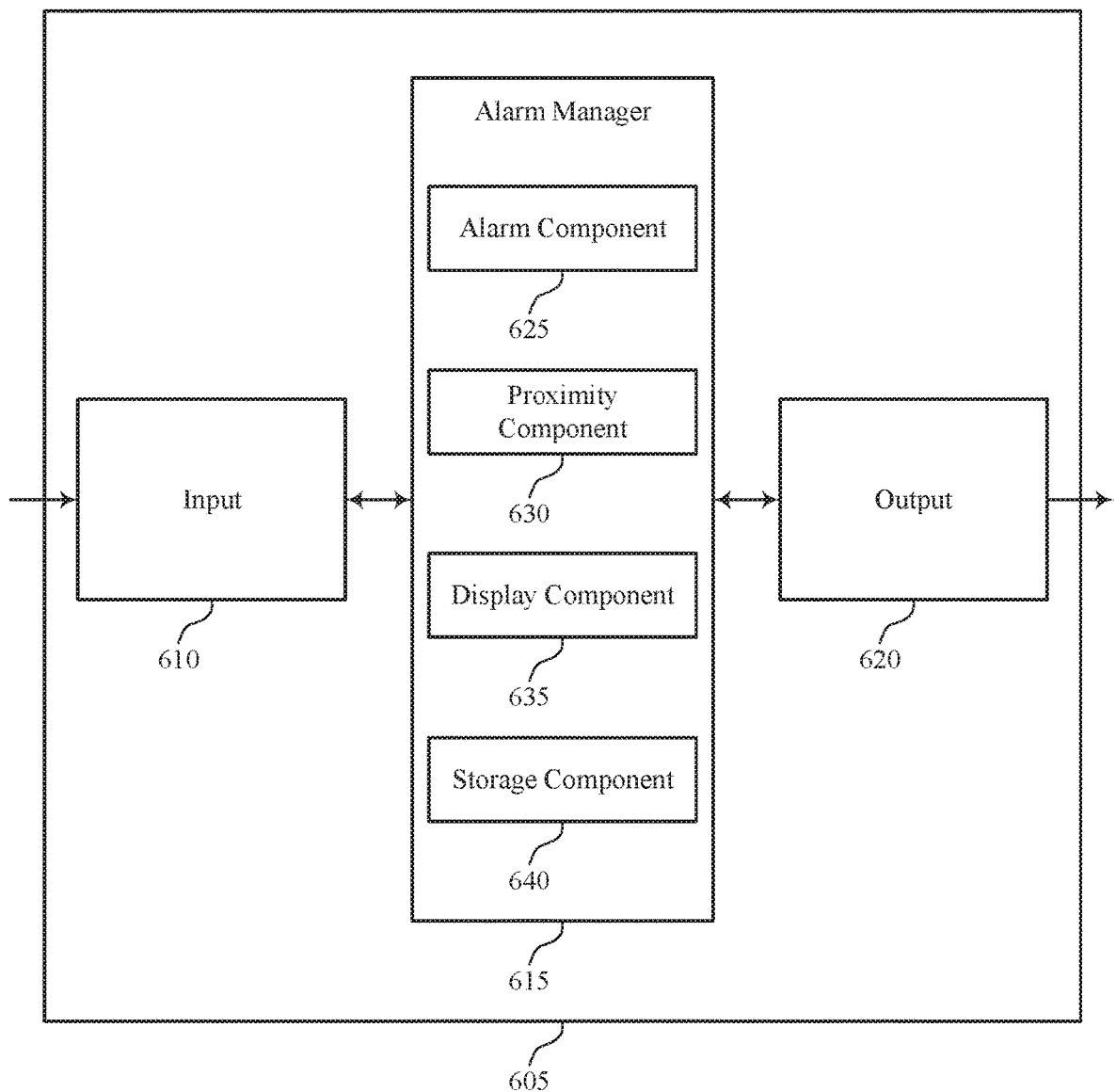

FIG. 6 shows a block diagram 600 of a device 605 that supports closed loop alarm management in accordance with aspects of the present disclosure. Device 605 may be an example of aspects of a device 505 or a medical device as described with reference to FIG. 5. Device 605 may include input 610, alarm manager 615, and output 620. Device 605 may also include a processor. Each of these components may be in communication with one another (e.g., via one or more buses).

Alarm manager 615 may be an example of aspects of the alarm manager 515 described with reference to FIG. 5.

Alarm manager 615 may also include alarm component 625, proximity component 630, display component 635, and storage component 640.

Alarm component 625 may receive, at a medical device, an alarm indication associated with a default alarm threshold for a measured physiological parameter. Alarm component 625 may also receive, at the medical device, a subsequent alarm indication associated with the default alarm threshold for the measured physiological parameter. In some cases, alarm component 625 may alarm according to the default alarm threshold if the subsequent alarm indication is present when a duration of the timer expires. In some examples, alarm component 625 may transmit the alarm message to a central server based on receiving the alarm indication.

Proximity component 630 may detect that a clinician is accessing the medical device in response to the alarm indication. Proximity component 630 may also detect that the clinician is within a proximity threshold of the medical device. Proximity component 630 may detect that the clinician is within the proximity threshold of the medical device by detecting near field communications signaling, detecting Bluetooth signaling, detecting imaging signaling of the clinician, or a combination thereof.

Display component 635 may display an alarm message associated with the alarm indication based on the detecting, refrain from displaying an alarm message associated with the subsequent alarm indication based on the modified alarm threshold, and lock a display screen of the medical device based on detecting that the clinician exceeded the proximity threshold of the medical device. In some cases, displaying the alarm message includes unlocking a display screen of the medical device based on the detecting that the clinician is within the proximity threshold of the medical device.

Storage component 640 may store an intervention action associated with an action of the clinician in response to the alarm indication. In some cases, the intervention action includes a routine check, a no action message, or an action message.

Figure 7:
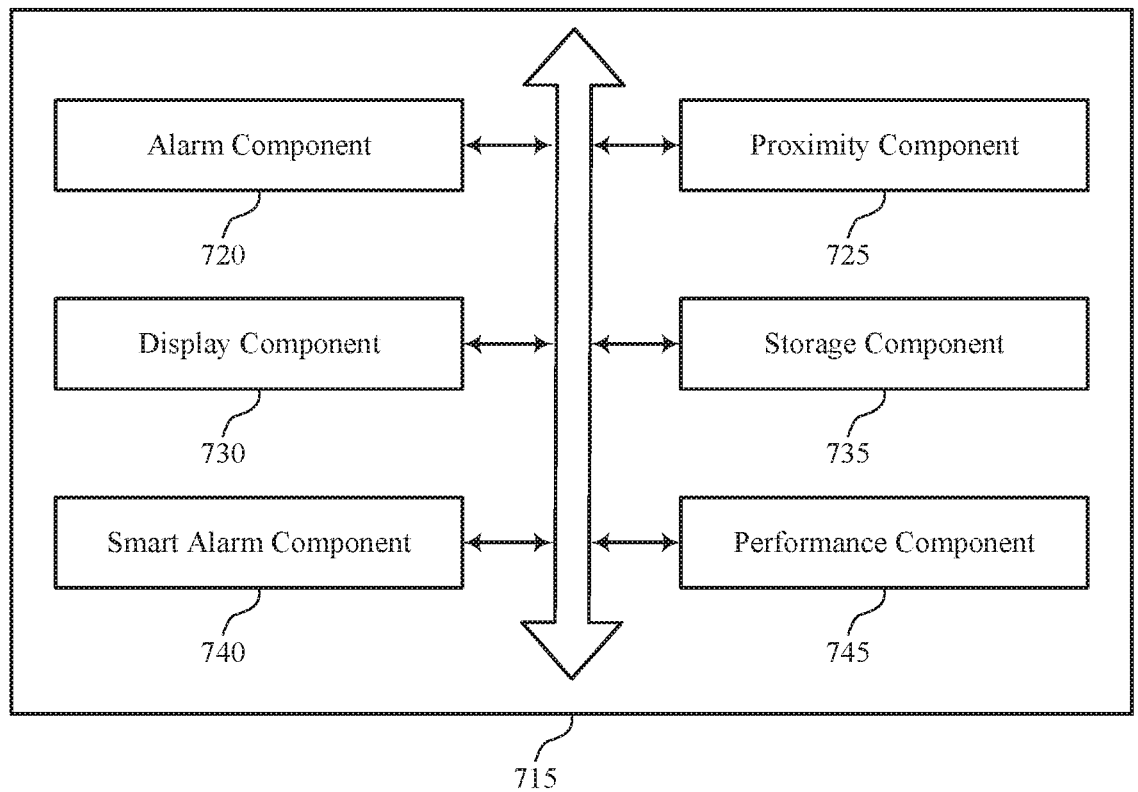

FIG. 7 shows a block diagram 700 of an alarm manager 715 that supports closed loop alarm management in accordance with aspects of the present disclosure. The alarm manager 715 may be an example of aspects of an alarm manager 515 or an alarm manager 615 described with reference to FIGS. 5 and 6. The alarm manager 715 may include alarm component 720, proximity component 725, display component 730, storage component 735, smart alarm component 740, and performance component 745. Each of these modules may communicate, directly or indirectly, with one another (e.g., via one or more buses).

Alarm component 720 may receive, at a medical device, an alarm indication associated with a default alarm threshold for a measured physiological parameter. Alarm component 720 may also receive, at the medical device, a subsequent alarm indication associated with the default alarm threshold for the measured physiological parameter. In some cases, alarm component 720 may alarm according to the default alarm threshold if the subsequent alarm indication is present when a duration of the timer expires. In some examples, alarm component 720 may transmit the alarm message to a central server based on receiving the alarm indication.

Proximity component 725 may detect that a clinician is accessing the medical device in response to the alarm indication. Proximity component 725 may also detect that the clinician is within a proximity threshold of the medical device. Proximity component 725 may detect that the clinician is within the proximity threshold of the medical device by detecting near field communications signaling, detecting Bluetooth signaling, detecting imaging signaling of the clinician, or a combination thereof.

Display component 730 may display an alarm message associated with the alarm indication based on the detecting, refrain from displaying an alarm message associated with the subsequent alarm indication based on the modified alarm threshold, and lock a display screen of the medical device based on detecting that the clinician exceeded the proximity threshold of the medical device. In some cases, displaying the alarm message includes unlocking a display screen of the medical device based on the detecting that the clinician is within the proximity threshold of the medical device.

Storage component 735 may store an intervention action associated with an action of the clinician in response to the alarm indication. In some cases, the intervention action includes a routine check, a no action message, or an action message.

Smart alarm component 740 may aggregate a set of intervention actions stored in response to a set of alarm indications associated with the default alarm threshold of the measured physiological parameter. In some cases, smart alarm component 740 may determine a first range of values of the measured physiological parameter associated with a first type of intervention action of the set of intervention actions and determine a second range of values of the measured physiological parameter associated with a second type of intervention action of the set of intervention actions. In some examples, smart alarm component 740 may determine an amount of reduction of a number of instances of the second type of intervention action in the second range of values based on modifying the default alarm threshold to a modified alarm threshold. Smart alarm component 740 may also determine an effect of modifying the default alarm threshold to the modified alarm threshold based on determining the amount of reduction of the number of instances of the second type of intervention action. In some examples, smart alarm component 740 may start a timer after detecting the subsequent alarm indication. In some cases, the first type of intervention action includes an action message and the second type of intervention action includes a no action message. In some cases, the aggregated set of intervention actions includes a histogram, where the histogram includes information related to an alarm type and an intervention action type.

Performance component 745 may determine performance information associated with the clinician based on the aggregated set of intervention actions. In some cases, the performance information includes a response time, an efficiency of the clinician, a service level report, a staff roster report, or a combination thereof.

Figure 8:
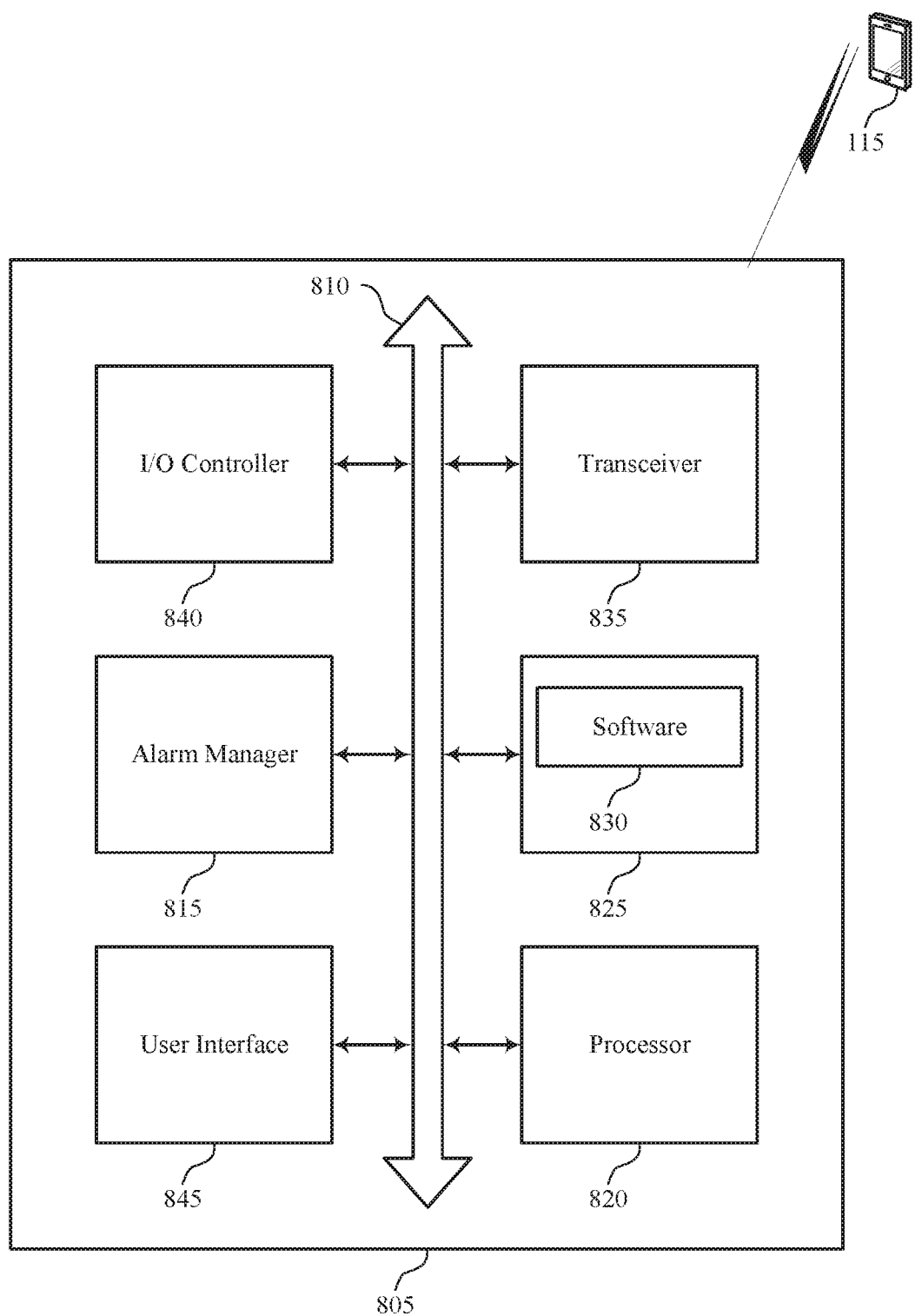
FIG. 8 illustrates a block diagram of a system including a medical device that supports closed loop alarm management in accordance with aspects of the present disclosure.

FIG. 8 shows a diagram of a system 800 including a device 805 that supports closed loop alarm management in accordance with aspects of the present disclosure. Device 805 may be an example of or include the components of device 505 or device 605 as described above, e.g., with reference to FIGS. 5 and 6. Device 805 may include components for bi-directional voice and data communications including components for transmitting and receiving communications, including alarm manager 815, processor 820, memory 825, software 830, transceiver 835, I/O controller 840, and user interface 845. These components may be in electronic communication via one or more buses (e.g., bus 810).

Processor 820 may include an intelligent hardware device, (e.g., a general-purpose processor, a DSP, a central processing unit (CPU), a microcontroller, an ASIC, an FPGA, a programmable logic device, a discrete gate or transistor logic component, a discrete hardware component, or any combination thereof). In some cases, processor 820 may be configured to operate a memory array using a memory controller. In other cases, a memory controller may be integrated into processor 820. Processor 820 may be configured to execute computer-readable instructions stored in a memory to perform various functions (e.g., functions or tasks supporting closed loop alarm management).

Memory 825 may include random access memory (RAM) and read only memory (ROM). The memory 825 may store computer-readable, computer-executable software 830 including instructions that, when executed, cause the processor to perform various functions described herein. In some cases, the memory 825 may contain, among other things, a basic input/output system (BIOS) which may control basic hardware or software operation such as the interaction with peripheral components or devices.

Software 830 may include code to implement aspects of the present disclosure, including code to support closed loop alarm management. Software 830 may be stored in a non-transitory computer-readable medium such as system memory or other memory. In some cases, the software 830 may not be directly executable by the processor but may cause a computer (e.g., when compiled and executed) to perform functions described herein.

Transceiver 835 may communicate bi-directionally, via one or more antennas, wired, or wireless links as described above. For example, the transceiver 835 may represent a wireless transceiver and may communicate bi-directionally with another wireless transceiver. The transceiver 835 may also include a modem to modulate the packets and provide the modulated packets to the antennas for transmission, and to demodulate packets received from the antennas.

I/O controller 840 may manage input and output signals for device 805. I/O controller 840 may also manage peripherals not integrated into device 805. In some cases, I/O controller 840 may represent a physical connection or port to an external peripheral. In some cases, I/O controller 840 may utilize an operating system such as iOS®, ANDROID®, MS-DOS®, MS-WINDOWS®, OS/2®, UNIX®, LINUX®, or another known operating system. In other cases, I/O controller 840 may represent or interact with a modem, a keyboard, a mouse, a touchscreen, or a similar device. In some cases, I/O controller 840 may be implemented as part of a processor. In some cases, a user may interact with device 805 via I/O controller 840 or via hardware components controlled by I/O controller 840.

User interface 845 may enable a user to interact with device 805. In some aspects, the user interface module 845 may include an audio device, such as an external speaker system, an external display device such as a display screen, or an input device (e.g., remote control device interfaced with the user interface module 845 directly or through the I/O controller module).

Figure 9:
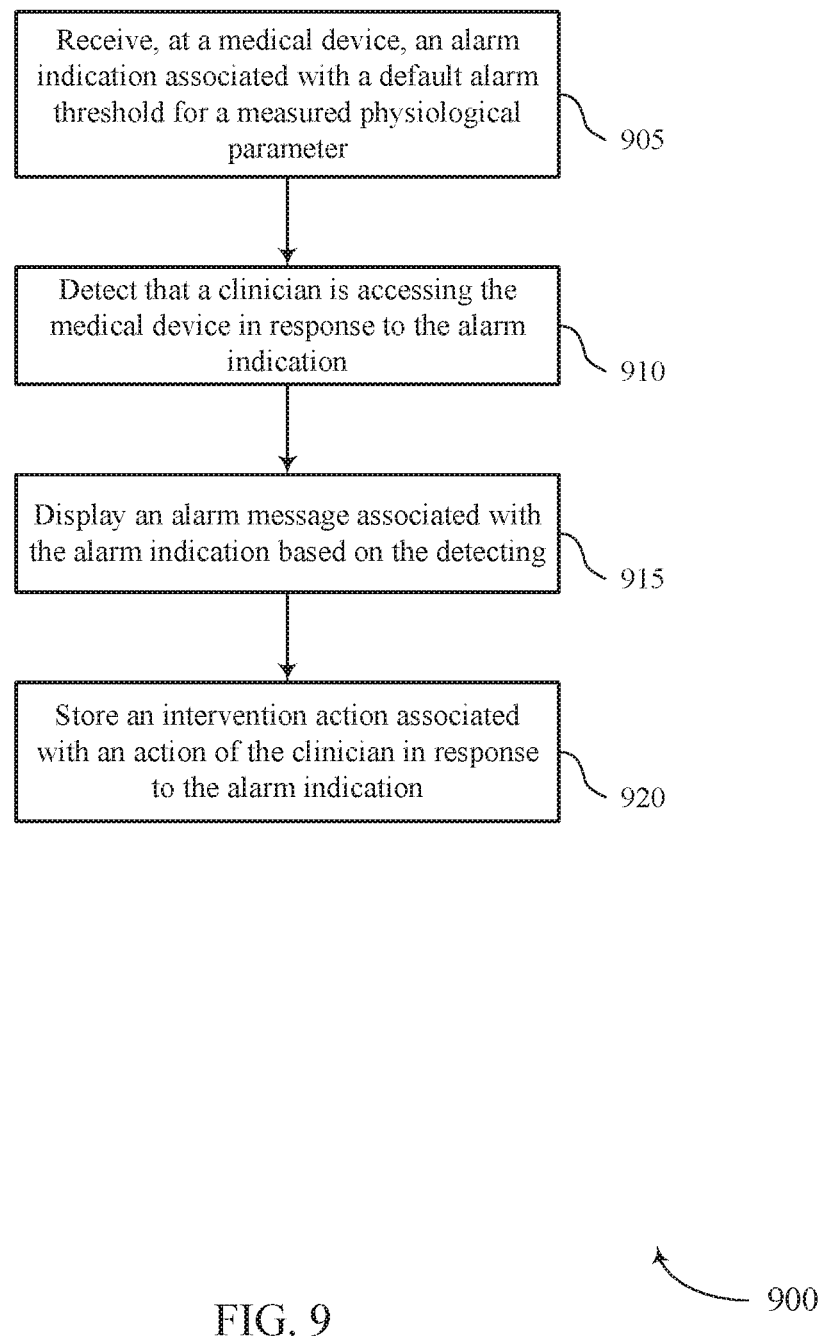
FIGS. 9 through 12 illustrate methods for closed loop alarm management in accordance with aspects of the present disclosure.

FIG. 9 shows a flowchart illustrating a method 900 for closed loop alarm management in accordance with aspects of the present disclosure. The operations of method 900 may be implemented by a medical device or its components as described herein. For example, the operations of method 900 may be performed by an alarm manager as described with reference to FIGS. 5 through 8. In some examples, a medical device may execute a set of codes to control the functional elements of the device to perform the functions described below. Additionally or alternatively, the medical device may perform aspects of the functions described below using special-purpose hardware.

At 905 the medical device may receive, at a medical device, an alarm indication associated with a default alarm threshold for a measured physiological parameter. The operations of 905 may be performed according to the methods described herein. In certain examples, aspects of the operations of 905 may be performed by an alarm component as described with reference to FIGS. 6 and 7.

At 910 the medical device may detect that a clinician is accessing the medical device in response to the alarm indication. In some cases, the medical device may detect that a clinician is within a proximity threshold of the medical device. The operations of 910 may be performed according to the methods described herein. In certain examples, aspects of the operations of 910 may be performed by a proximity component as described with reference to FIGS. 6 and 7.

At 915 the medical device may display an alarm message associated with the alarm indication based at least in part on the detecting. The operations of 915 may be performed according to the methods described herein. In certain examples, aspects of the operations of 915 may be performed by a display component as described with reference to FIGS. 6 and 7.

At 920 the medical device may store an intervention action associated with an action of the clinician in response to the alarm indication. The operations of 920 may be performed according to the methods described herein. In certain examples, aspects of the operations of 920 may be performed by a storage component as described with reference to FIGS. 6 and 7.

Figure 10:
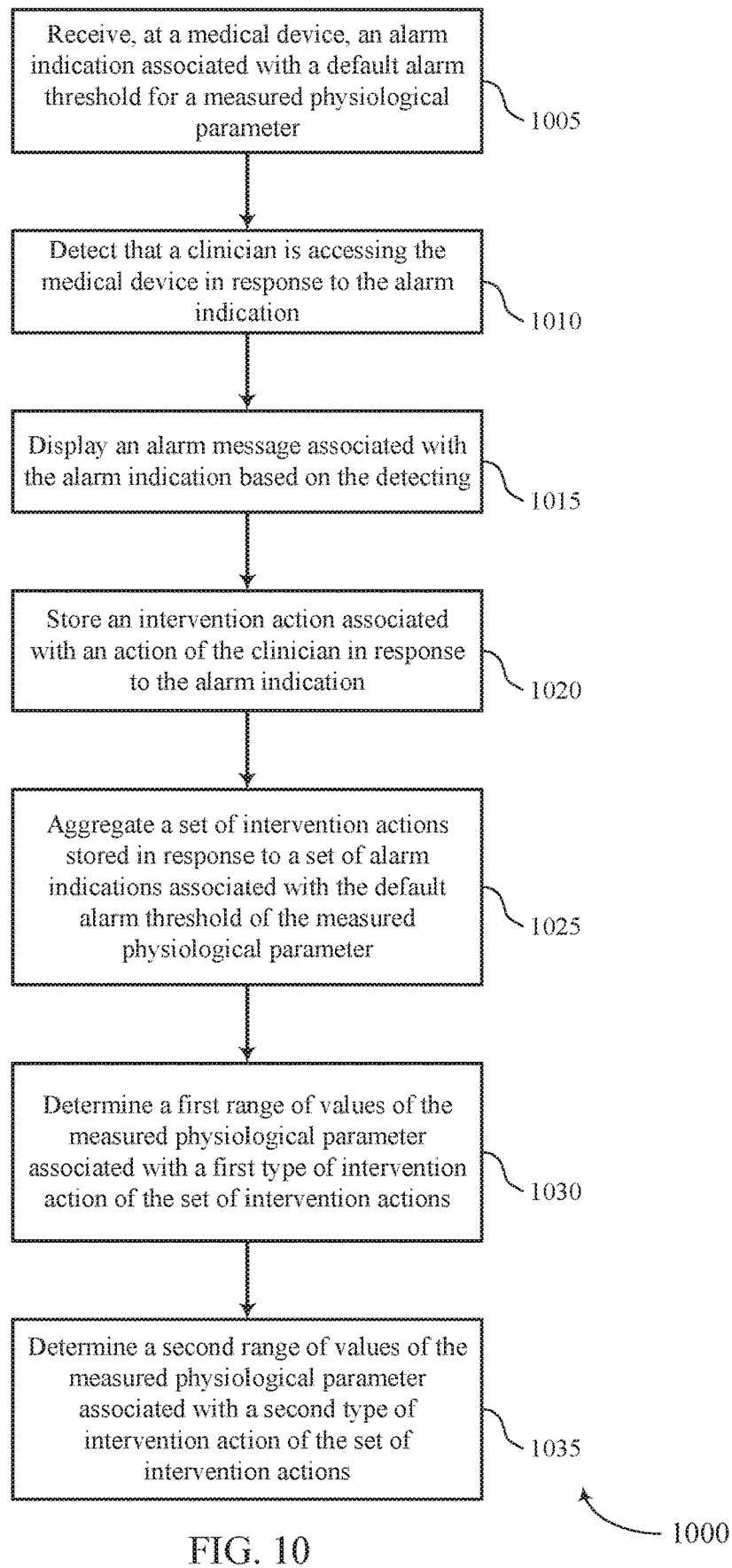

FIG. 10 shows a flowchart illustrating a method 1000 for closed loop alarm management in accordance with aspects of the present disclosure. The operations of method 1000 may be implemented by a medical device or its components as described herein. For example, the operations of method 1000 may be performed by an alarm manager as described with reference to FIGS. 5 through 8. In some examples, a medical device may execute a set of codes to control the functional elements of the device to perform the functions described below. Additionally or alternatively, the medical device may perform aspects of the functions described below using special-purpose hardware.

At 1005 the medical device may receive, at a medical device, an alarm indication associated with a default alarm threshold for a measured physiological parameter. The operations of 1005 may be performed according to the methods described herein. In certain examples, aspects of the operations of 1005 may be performed by an alarm component as described with reference to FIGS. 6 and 7.

At 1010 the medical device may detect that a clinician is accessing the medical device in response to the alarm indication. In some cases, the medical device may detect that a clinician is within a proximity threshold of the medical device. The operations of 1010 may be performed according to the methods described herein. In certain examples, aspects of the operations of 1010 may be performed by a proximity component as described with reference to FIGS. 6 and 7.

At 1015 the medical device may display an alarm message associated with the alarm indication based at least in part on the detecting. The operations of 1015 may be performed according to the methods described herein. In certain examples, aspects of the operations of 1015 may be performed by a display component as described with reference to FIGS. 6 and 7.

At 1020 the medical device may store an intervention action associated with an action of the clinician in response to the alarm indication. The operations of 1020 may be performed according to the methods described herein. In certain examples, aspects of the operations of 1020 may be performed by a storage component as described with reference to FIG. 7.

At 1025 the medical device may aggregate a plurality of intervention actions stored in response to a plurality of alarm indications associated with the default alarm threshold of the measured physiological parameter. The operations of 1025 may be performed according to the methods described herein. In certain examples, aspects of the operations of 1025 may be performed by a smart alarm component as described with reference to FIG. 7.

At 1030 the medical device may determine a first range of values of the measured physiological parameter associated with a first type of intervention action of the plurality of intervention actions. The operations of 1030 may be performed according to the methods described herein. In certain examples, aspects of the operations of 1030 may be performed by a smart alarm component as described with reference to FIG. 7.

At 1035 the medical device may determine a second range of values of the measured physiological parameter associated with a second type of intervention action of the plurality of intervention actions. The operations of 1035 may be performed according to the methods described herein. In certain examples, aspects of the operations of 1035 may be performed by a smart alarm component as described with reference to FIG. 7.

Figure 11:
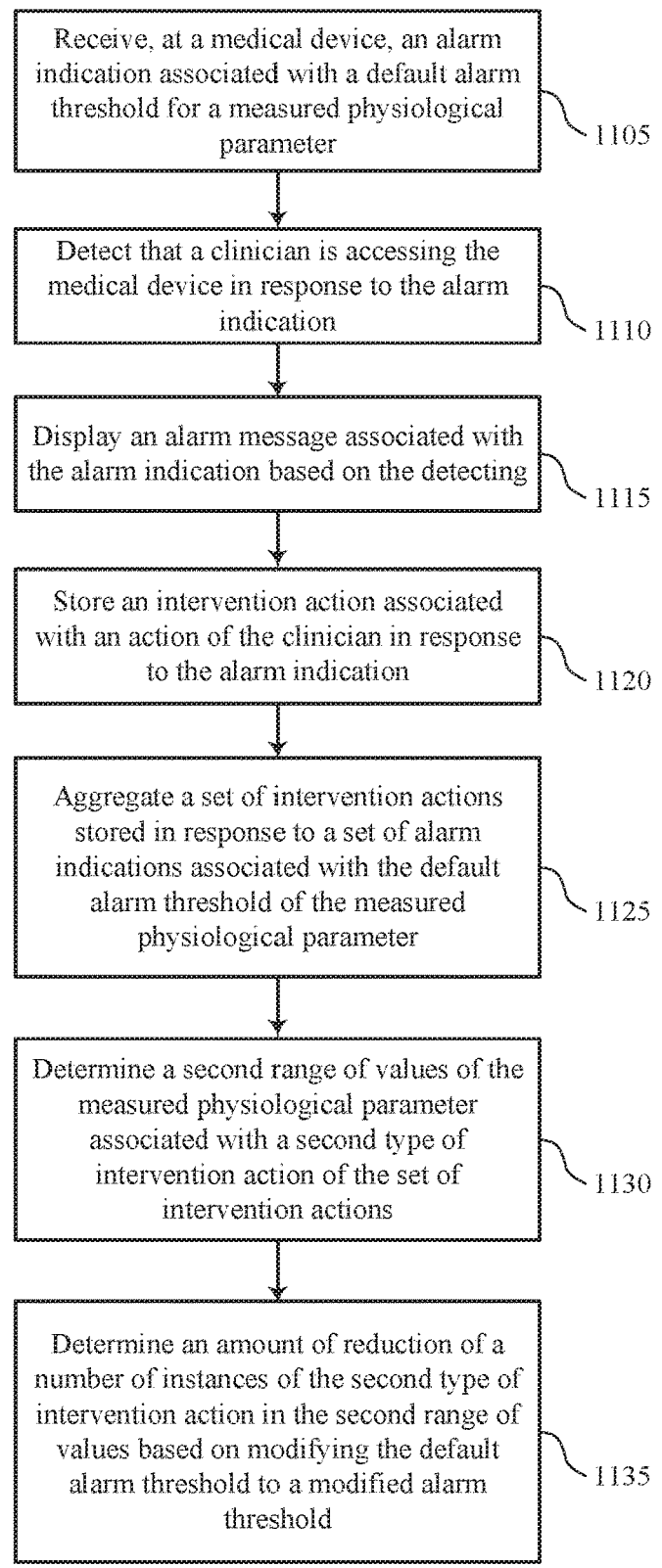

FIG. 11 shows a flowchart illustrating a method 1100 for closed loop alarm management in accordance with aspects of the present disclosure. The operations of method 1100 may be implemented by a medical device or its components as described herein. For example, the operations of method 1100 may be performed by an alarm manager as described with reference to FIGS. 5 through 8. In some examples, a medical device may execute a set of codes to control the functional elements of the device to perform the functions described below. Additionally or alternatively, the medical device may perform aspects of the functions described below using special-purpose hardware.

At 1105 the medical device may receive, at a medical device, an alarm indication associated with a default alarm threshold for a measured physiological parameter. The operations of 1105 may be performed according to the methods described herein. In certain examples, aspects of the operations of 1105 may be performed by an alarm component as described with reference to FIGS. 6 and 7.

At 1110 the medical device may detect that a clinician is accessing the medical device in response to the alarm indication. In some cases, the medical device may detect that a clinician is within a proximity threshold of the medical device. The operations of 1110 may be performed according to the methods described herein. In certain examples, aspects of the operations of 1110 may be performed by a proximity component as described with reference to FIGS. 6 and 7.

At 1115 the medical device may display an alarm message associated with the alarm indication based at least in part on the detecting. The operations of 1115 may be performed according to the methods described herein. In certain examples, aspects of the operations of 1115 may be performed by a display component as described with reference to FIGS. 6 and 7.

At 1120 the medical device may store an intervention action associated with an action of the clinician in response to the alarm indication. The operations of 1120 may be performed according to the methods described herein. In certain examples, aspects of the operations of 1120 may be performed by a storage component as described with reference to FIG. 7.

At 1125 the medical device may aggregate a plurality of intervention actions stored in response to a plurality of alarm indications associated with the default alarm threshold of the measured physiological parameter. The operations of 1125 may be performed according to the methods described herein. In certain examples, aspects of the operations of 1125 may be performed by a smart alarm component as described with reference to FIG. 7.

At 1130 the medical device may determine a second range of values of the measured physiological parameter associated with a second type of intervention action of the plurality of intervention actions. The operations of 1130 may be performed according to the methods described herein. In certain examples, aspects of the operations of 1130 may be performed by a smart alarm component as described with reference to FIG. 7.

At 1135 the medical device may determine an amount of reduction of a number of instances of the second type of intervention action in the second range of values based at least in part on modifying the default alarm threshold to a modified alarm threshold. The operations of 1135 may be performed according to the methods described herein. In certain examples, aspects of the operations of 1135 may be performed by a smart alarm component as described with reference to FIG. 7.

Figure 12:
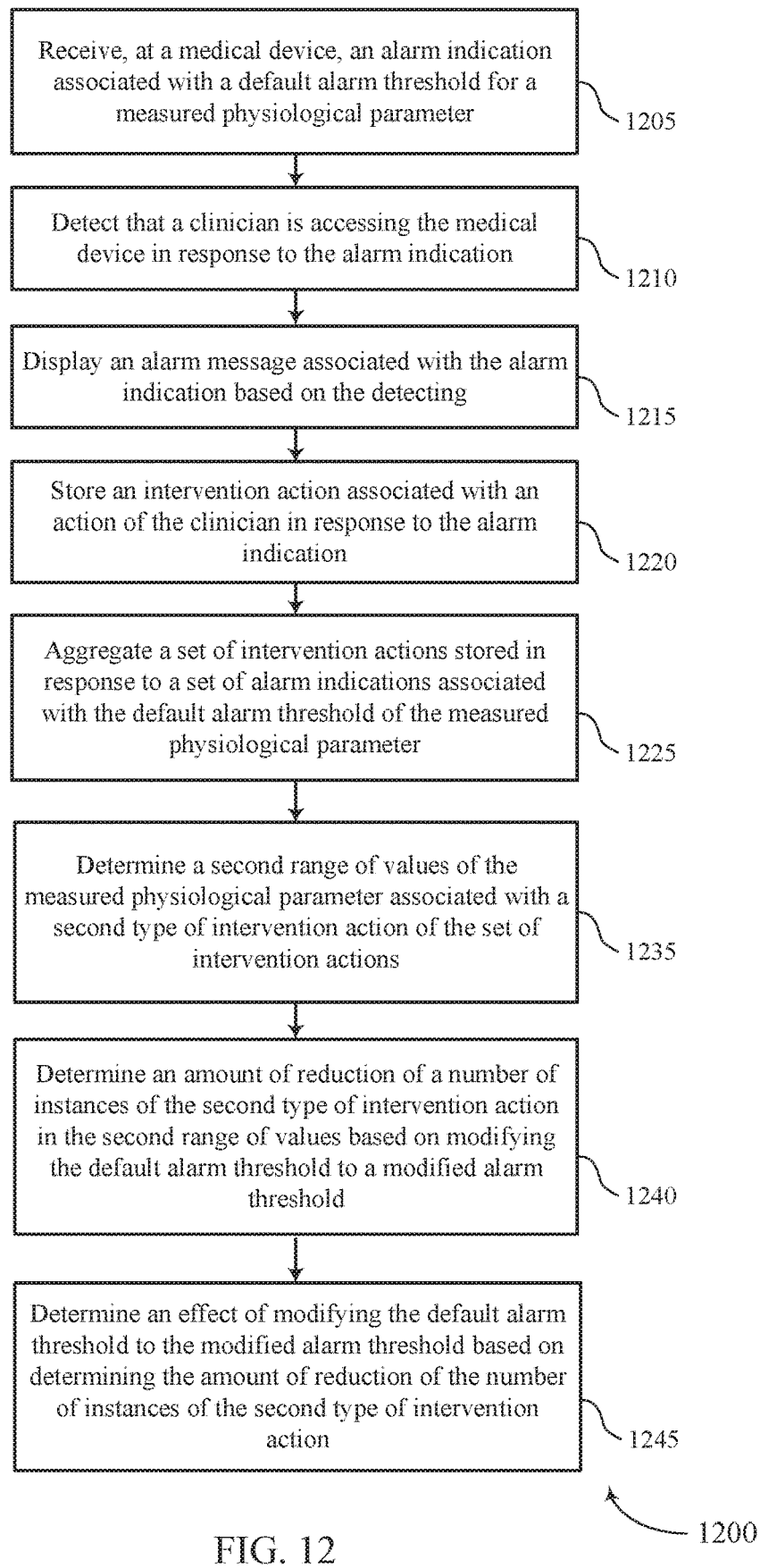

FIG. 12 shows a flowchart illustrating a method 1200 for closed loop alarm management in accordance with aspects of the present disclosure. The operations of method 1200 may be implemented by a medical device or its components as described herein. For example, the operations of method 1200 may be performed by an alarm manager as described with reference to FIGS. 5 through 8. In some examples, a medical device may execute a set of codes to control the functional elements of the device to perform the functions described below. Additionally or alternatively, the medical device may perform aspects of the functions described below using special-purpose hardware.

At 1205 the medical device may receive, at a medical device, an alarm indication associated with a default alarm threshold for a measured physiological parameter. The operations of 1205 may be performed according to the methods described herein. In certain examples, aspects of the operations of 1205 may be performed by an alarm component as described with reference to FIGS. 6 and 7.

At 1210 the medical device may detect that a clinician is accessing the medical device in response to the alarm indication. In some cases, the medical device may detect that a clinician is within a proximity threshold of the medical device. The operations of 1210 may be performed according to the methods described herein. In certain examples, aspects of the operations of 1210 may be performed by a proximity component as described with reference to FIGS. 6 and 7.

At 1215 the medical device may display an alarm message associated with the alarm indication based at least in part on the detecting. The operations of 1215 may be performed according to the methods described herein. In certain examples, aspects of the operations of 1215 may be performed by a display component as described with reference to FIGS. 6 and 7.

At 1220 the medical device may store an intervention action associated with an action of the clinician in response to the alarm indication. The operations of 1220 may be performed according to the methods described herein. In certain examples, aspects of the operations of 1220 may be performed by a storage component as described with reference to FIG. 7.

At 1225 the medical device may aggregate a plurality of intervention actions stored in response to a plurality of alarm indications associated with the default alarm threshold of the measured physiological parameter. The operations of 1225 may be performed according to the methods described herein. In certain examples, aspects of the operations of 1225 may be performed by a smart alarm component as described with reference to FIG. 7.

At 1230 the medical device may determine a second range of values of the measured physiological parameter associated with a second type of intervention action of the plurality of intervention actions. The operations of 1230 may be performed according to the methods described herein. In certain examples, aspects of the operations of 1230 may be performed by a smart alarm component as described with reference to FIG. 7.

At 1235 the medical device may determine an amount of reduction of a number of instances of the second type of intervention action in the second range of values based at least in part on modifying the default alarm threshold to a modified alarm threshold. The operations of 1235 may be performed according to the methods described herein. In certain examples, aspects of the operations of 1235 may be performed by a smart alarm component as described with reference to FIG. 7.

At 1240 the medical device may determine an effect of modifying the default alarm threshold to the modified alarm threshold based at least in part on determining the amount of reduction of the number of instances of the second type of intervention action. The operations of 1240 may be performed according to the methods described herein. In certain examples, aspects of the operations of 1240 may be performed by a smart alarm component as described with reference to FIG. 7.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for patient monitoring, comprising:
    receiving, at a medical device, an alarm indication associated with a default alarm threshold for a measured physiological parameter;
    detecting that a clinician is accessing the medical device in response to the alarm indication;
    displaying an alarm message associated with the alarm indication based at least in part on the detecting; and
    storing a plurality of intervention actions associated with an action of the clinician in response to the alarm indication;
    determining a first range of values of the measured physiological parameter associated with a plurality of first intervention actions of the plurality of intervention actions, the plurality of first intervention actions indicating that the clinician performed a medical action in response to the alarm indication;
    determining a second range of values of the measured physiological parameter associated with a plurality of second intervention actions of the plurality of intervention actions, the plurality of second intervention actions indicating that the clinician silenced the alarm indication and performed no medical action in response to the alarm indication; and
    displaying the first range of values, the second range of values, a transition line between the first range of values and the second range of values, an indicator in the first range of values for each of the plurality of first intervention actions, and an indicator in the second range of values for each of the plurality of second intervention actions.

2. The method of claim 1, further comprising:
    detecting that the clinician is within a proximity threshold of the medical device, wherein displaying the alarm message is based at least in part on the detection.

3. The method of claim 1, further comprising:
    aggregating the plurality of intervention actions stored in response to a plurality of alarm indications associated with the default alarm threshold of the measured physiological parameter.

4. The method of claim 3, further comprising:
    determining an amount of reduction of a number of instances of the plurality of second intervention actions in the second range of values based at least in part on modifying the default alarm threshold to a modified alarm threshold, the modified alarm threshold corresponding to the transition line between the first range of values and the second range of values.

5. The method of claim 4, further comprising:
    determining an effect of modifying the default alarm threshold to the modified alarm threshold based at least in part on determining the amount of reduction of the number of instances of the plurality of second intervention actions.

6. The method of claim 5, further comprising:
    receiving, at the medical device, a subsequent alarm indication associated with the default alarm threshold for the measured physiological parameter; and
    refraining from displaying an alarm message associated with the subsequent alarm indication based at least in part on the modified alarm threshold.

7. The method of claim 6, further comprising:
    starting a timer after detecting the subsequent alarm indication; and
    alarming according to the default alarm threshold if the subsequent alarm indication is present when a duration of the timer expires.

8. The method of claim 3, wherein the plurality of first intervention actions comprises an action message and the plurality of second intervention actions comprises a no action message.

9. The method of claim 3, wherein the aggregated plurality of intervention actions comprises a histogram, wherein the histogram comprises the first range of values, the second range of values, the transition line, the indicator in the first range of values, the indicator in the second range of values, and information related to an alarm type.

10. The method of claim 3, further comprising:
    determining performance information associated with the clinician based at least in part on the aggregated plurality of intervention actions.

11. The method of claim 10, wherein the performance information comprises a response time, an efficiency of the clinician, a service level report, a staff roster report, or a combination thereof.

12. The method of claim 2, wherein displaying the alarm message comprises:
    unlocking a display screen of the medical device based at least in part on the detecting that the clinician is within the proximity threshold of the medical device.

13. The method of claim 2, further comprising:
    locking a display screen of the medical device based at least in part on detecting that the clinician exceeded the proximity threshold of the medical device.

14. The method of claim 1, wherein the plurality of intervention actions comprise a routine check, a no action message, or an action message.

15. The method of claim 2, further comprising:
detecting that the clinician is within the proximity threshold of the medical device comprises detecting near field communications signaling, detecting Bluetooth signaling, detecting imaging signaling of the clinician, or a combination thereof.

16. A medical device for patient monitoring, comprising:
a processor;
memory in electronic communication with the processor; and
instructions stored in the memory and operable, when executed by the processor, to cause the medical device to:
receive, at the medical device, an alarm indication associated with a default alarm threshold for a measured physiological parameter;
detect that a clinician is accessing the medical device in response to the alarm indication;
display an alarm message associated with the alarm indication based at least in part on the detecting; and
store a plurality of intervention actions associated with an action of the clinician in response to the alarm indication;
determine a first range of values of the measured physiological parameter associated with a plurality of first intervention actions of the plurality of intervention actions, the plurality of first intervention actions indicating that the clinician performed a medical action in response to the alarm indication; and
determine a second range of values of the measured physiological parameter associated with a plurality of second intervention actions of the plurality of intervention actions, the plurality of second intervention actions indicating that the clinician silenced the alarm indication and performed no medical action in response to the alarm indication; and
display the first range of values, the second range of values, a transition line between the first range of values and the second range of values, an indicator in the first range of values for each of the plurality of first intervention actions, and an indicator in the second range of values for each of the plurality of second intervention actions.

17. The medical device of claim 16, wherein the instructions stored in the memory comprise instructions operable to cause the medical device to:
aggregate the plurality of intervention actions stored in response to a plurality of alarm indications associated with the default alarm threshold of the measured physiological parameter.

18. The medical device of claim 17, wherein the instructions stored in the memory comprise instructions operable to cause the medical device to:
determine an amount of reduction of a number of instances of the plurality of second intervention actions in the second range of values based at least in part on modifying the default alarm threshold to a modified alarm threshold, the modified alarm threshold corresponding to the transition line between the first range of values and the second range of values.

19. The medical device of claim 18, wherein the instructions stored in the memory comprise instructions operable to cause the medical device to:
determine an effect of modifying the default alarm threshold to the modified alarm threshold based at least in part on determining the amount of reduction of the number of instances of the plurality of second intervention actions.

20. A non-transitory computer readable medium storing code for patient monitoring, the code comprising instructions executable by a processor to:
receive, at a medical device, an alarm indication associated with a default alarm threshold for a measured physiological parameter;
detect that a clinician is accessing the medical device in response to the alarm indication;
display an alarm message associated with the alarm indication based at least in part on the detecting; and
store a plurality of intervention actions associated with an action of the clinician in response to the alarm indication;
determine a first range of values of the measured physiological parameter associated with a plurality of first intervention actions of the plurality of intervention actions, the plurality of first intervention actions indicating that the clinician performed a medical action in response to the alarm indication; and
determine a second range of values of the measured physiological parameter associated with a plurality of second intervention actions of the plurality of intervention actions, the plurality of second intervention actions indicating that the clinician silenced the alarm indication and performed no medical action in response to the alarm indication; and
display the first range of values, the second range of values, a transition line between the first range of values and the second range of values, an indicator in the first range of values for each of the plurality of first intervention actions, and an indicator in the second range of values for each of the plurality of second intervention actions.

* * * * *